United States Patent [19]

Hasegawa et al.

[11] Patent Number: 4,550,080
[45] Date of Patent: Oct. 29, 1985

[54] PROCESS FOR THE PREPARATION OF A PLASMINOGEN ACTIVATOR

[75] Inventors: Akio Hasegawa, Numazu; Hiroshige Kojima, Fuji, both of Japan

[73] Assignee: Asahi Kasei Kogyo Kabushiki Kaisha, Osaka, Japan

[21] Appl. No.: 617,452

[22] Filed: Jun. 5, 1984

[51] Int. Cl.4 ............................................. C12N 9/48
[52] U.S. Cl. ................................................... 435/212
[58] Field of Search ...:.......................... 435/212, 215

[56] References Cited

U.S. PATENT DOCUMENTS

| | | | |
|---|---|---|---|
| 3,904,480 | 9/1975 | Hull et al. | 435/217 |
| 4,190,708 | 2/1980 | Kuo et al. | 435/215 |
| 4,232,124 | 11/1980 | Mann | 435/212 |
| 4,317,882 | 3/1982 | Horiguchi et al. | 435/212 |
| 4,505,893 | 3/1985 | Mori et al. | 424/94 |

FOREIGN PATENT DOCUMENTS 100982  2/1984  European Pat. Off. .
2104081  3/1983  United Kingdom ................ 435/215

*Primary Examiner*—Lionel M. Shapiro
*Attorney, Agent, or Firm*—Sughrue, Mion, Zinn, Macpeak, and Seas

[57] ABSTRACT

A process for the preparation of a plasminogen activator is described, which comprises bringing normal diploid cells derived from human bodies capable of producing the plasminogen activator into contact with a solution containing an enzymatically-decomposed animal meat peptone, the plasminogen activator having the following properties:

(a) molecular weight: 63,000±10,000;
(b) isoelectric point: 7.0 to 8.5;
(c) affinity to fibrin: present;
(d) affinity to Concanavalin A: present;
(e) optimum pH: 7 to 9.5; and
(f) no reactivity with anti-urokinase specific antibody.

The plasminogen activator can be obtained in a high yield.

6 Claims, 2 Drawing Figures

PROCESS FOR THE PREPARATION OF A PLASMINOGEN ACTIVATOR

FIELD OF THE INVENTION

This invention relates to a process for the preparation of a plasminogen activator in a high yield by the use of normal diploid cells derived from human bodies.

BACKGROUND OF THE INVENTION

Urokinase separated and purified from urine or cultured kidney cells and streptokinase recovered from streptococci are nowadays practically used as plasminogen activators. Specifically, these plasminogen activators are used as thrombolytic agents.

However, it is known that these plasminogen activators are often administered to patients in large amounts in order to obtain necessary therapeutic effects overcoming their poorness in affinity with fibrin and thus cause side effects such as internal hemorrhage. Specifically, plasmin which is produced in circulating blood by these plasminogen activators tends to lose activity immediately upon combination with plasmin inhibitors in the blood. Accordingly, in order to exhibit the necessary therapeutic effects, these plasminogen activators must be administered in large amounts to produce plasmin, viz., in an amount exceeding that of the plasmin inhibitors in the blood. However, the production of a large amount of plasmin will decompose fibrinogen, resulting in hemorrhage. Accordingly, if a plasminogen activator which has a high affinity with fibrin and is capable of producing plasmin on fibrin can be obtained, it becomes possible to decompose fibrin with a small amount of the plasminogen activator without being subjected to the influence of plasmin inhibitors in circulating blood, and also to reduce the effects of decomposing fibrinogen. Therefore, it has been desired to provide a thrombolytic agent having a high affinity for fibrin which shows a high thrombolytic activity using a small amount thereof, and which has less side effects.

One of the inventors, with others, has already found a novel plasminogen activator having properties listed below in a culture liquid of normal diploid cells of human bodies and endeavored to put it in practical use (European patent application (OPI) No. 0100982).

(a) molecular weight: 63,000±10,000
(b) isoelectric point: 7.0 to 8.5
(c) affinity to fibrin: present
(d) affinity to Concanavalin A: present
(e) optimum pH: 7.0 to 9.5
(f) no reactivity with anti-urokinase specific antibody.

However, because of low productivity, this plasminogen activator has been difficult to provide in large amounts on an industrial scale.

SUMMARY OF THE INVENTION

As a result of concentrated studies to find an efficient process for the preparation of the plasminogen activator, it has now been found that the presence of a large amount of peptone derived by the enzymatic decomposition of animal meats in a solution which produces the plasminogen activator upon contact with normal diploid cells (i.e., cells having a normal diploid chromosome) derived from human bodies causes a drastic increase of the production of the activator. The present invention has been achieved on the basis of this discovery.

This invention is therefore a process for the preparation of a plasminogen activator which comprises bringing normal diploid cells derived from human bodies capable of producing a plasminogen activator into contact with a solution containing an enzymatically-decomposed animal meat peptone.

DETAILED DESCRIPTION OF THE INVENTION

Figure 1:
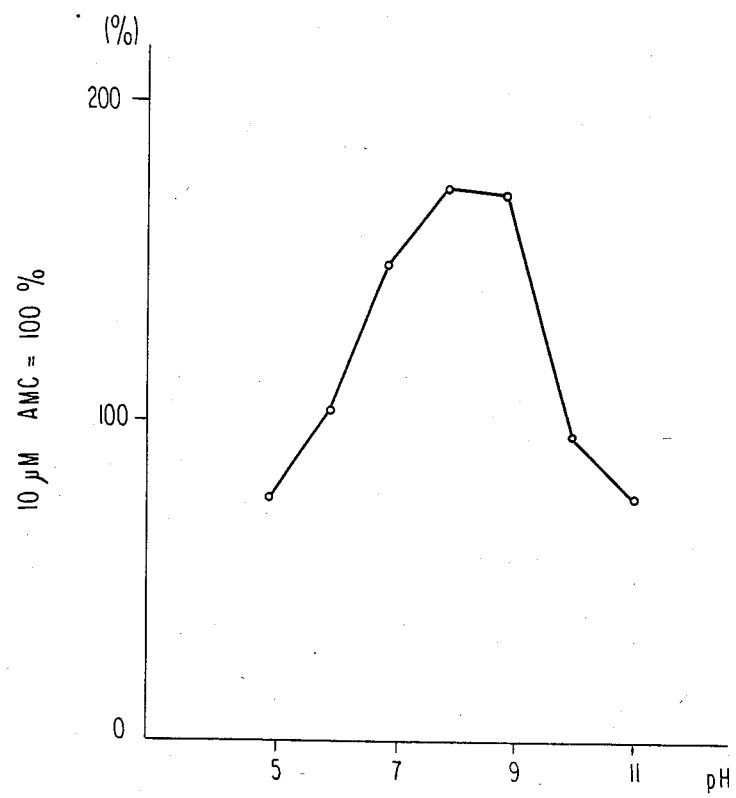
FIG. 1 is a graph showing the optimum pH of a plasminogen activator obtained by the invention.

The present invention is achieved by the use of normal diploid cells derived from human bodies capable of producing the plasminogen activator. As such normal diploid cells, there can be used, for example, cells derived from human kidney, intestines, lung, heart, ureter, skin, foreskin, tongue, thyroid gland, placenta and womb and cells derived from the whole embryo, more preferably cells derived from human lung or foreskin. The cells derived from human bodies described above herein include cells derived from fetus and neonate.

These cells can be proliferated in accordance with a normal method for the culture of animal cells, for example, as described in P. K. Kruse and M. K. Patterson, *Tissue Culture Methods and Applications*, pp. 220–223, Academic Press, New York, San Francisco, 1973, and thereafter they can be brought into contact with a solution containing a carbon source, a nitrogen source, and, if necessary, inorganic salts and/or other additives, to produce the plasminogen activator. As additives which are allowed to coexist in the solution, there can be used amino acids, vitamins, peptides, saccharides, and organic acids. Examples of such additives include the natural amino acids, p-aminobenzoic acid, D-biotin, calciferol, calcium D-panthotenate, cholesterol, choline chloride, folic acid, i-inositol, menadione, nicotinamide, nicotinic acid, pyridoxal, pyridoxine, riboflavin, thiamine, DL-α-tocopherol, Tween 80 (trademark of Kao Atlas for polyoxyethylene monooleate), vitamin A, adenine, ATP, AMP, deoxyribose, ribose, glutathione, guanine, thymine, hypoxanthine, uracil, xanthine, hydrolyzate of lactalbumine, polypeptone, hydrolyzate of casein, glucose, maltose, fructose, mannitol, dextran, fumaric acid, malic acid, oxalacetic acid, citric acid, succinic acid, pyruvic acid, NaCl, KCl, $MgCl_2$, $MgSO_4$, $NaH_2PO_4$, $Na_2HPO_4$, $KH_2PO_4$, $CuSO_4$, $Fe(NO_3)_3$, $FeSO_4$, $MnCl_2$, $(NH_4)_2MoO_4$, and $ZnSO_4$. The addition of the enzymatically-decomposed animal meat peptone in accordance with the present invention can drastically improve the yield of the plasminogen activator.

Mass culture on an industrial scale according to the present invention can be achieved by the use of roller bottle culture process, a multi-layer plate culture process, hollow fiber culture process, plastic bag culture process, and microcarrier culture process, as described in R. T. Acton and J. D. Lynn, *Cell Culture and Its Application*, pp. 191–216, Academic Press, New York, 1977. For mass culture on a greater scale, a microcarrier culture process is desirable.

As the peptone used in the present invention there may be employed so-called proteose peptone, protease peptone and meat peptone, which are typical bacterial culture medium. The process for the preparation of the peptone is well known in the art and can be performed in accordance with the method described in *Study of Bacterial Culture Medium,* Vol. 2, by Toshikazu Sakazaki, published by Naya Bookshop Co., Ltd., 1967. Examples of animal meats that can be used include internal organs of cattle, pig, chicken, sheep and whale, among which beef is most often used. Examples of the decomposition enzyme are trypsin, papain, pepsin and pancreatin. These animal meats are minced, mixed with water, and then adjusted with sodium carbonate or concentrated hydrochloric acid to the pH value suitable for the enzymatic decomposition. The pH in the enzymatic decomposition varies depending upon the kind of enzyme used, and it is generally 7 to 9 for trypsin, 5 to 7 papain, 2 to 4 for pepsin and 6 to 8 for pancreatin. Then an enzyme is added to the mixture. The mixture is then subjected to an enzymatic decomposition at a temperature of 20 to 40° C. for 1 to 20 days, usually at a temperature of 37° C. for 2 to 3 days. After being digested, the mixture is heated to a temperature of 100° C. or more to inactivate the decomposition enzyme and coagulate the undigested protein. The undigested protein thus coagulated is removed by filtration, and the filtrate is concentrated, dried, and pulverized. The concentration, drying and pulverization can be achieved by boiling and pulverizing or by concentrating at a low temperature in a vacuum device and pulverizing. Examples of commercially available peptone are Proteose Peptone, Proteose Peptone No. 2, Proteose Peptone No. 3, and Thiopeptone from Difco, Proteose Peptone and Peptone PL 46 from Oxoid, Thiotone from BBL and Proteose Peptone from Daigo Eiyo Kagaku Co., Ltd.

The added concentration of the peptone varies depending upon the type and concentration of cells employed, and amino acids, vitamins, peptides, saccharides and organic acids which are allowed to coexist therewith, but is preferably from 0.1 to 4% (wt/v) and more preferably 0.1 to 2% (wt/v).

As described above, there can be used as suitable peptone various peptones which are different in preparation method. These peptones can be used singly or in combination.

These peptones must be sterilized before being added to the solution. The sterilization can be achieved by directly sterilizing the peptone powder with ethylene oxide or $\gamma$-ray, by sterilizing a solution of the peptone powder in an autoclave, or by passing a solution of the peptone powder through a sterilization filter. The sterilization method is not specifically limited but is preferably achieved by heating at a temperature of 120° C. in an autoclave for 10 to 60 minutes.

The production of the plasminogen activator is normally carried out in 0.2 ml or more of a culture liquid per 100,000 cells at a temperature of 25° to 40° C., and preferably at 31° to 37° C., in the pH range of 6.0 to 8.0, and preferably 7.0 to 7.4 The maintenance of the above pH value can be achieved by the use of a buffer system of $CO_2/HCO_3^-$. However, if the cells produce a large amount of $CO_2$ or organic acid such as lactic acid which obstructs the maintenance of the above pH value, a buffer such as HEPES (N-2-hydroxyethylpiperazine-N'-2-ethane sulfonic acid) may be used. The production normally takes from 4 to 30 days, but may take more than 30 days. Since the production rate of the activator of the present invention is gradually decreased in the latter half of the production stage, the industrial production process employs the number of days which are the most efficient for the total production. The plasminogen activator is released from the cells into the culture liquid under the above conditions. The measurement of the yield of the activator was carried out as follows:

An agar-added fibrin plate prepared from a 95% coagulated fibrinogen (plasminogen content: about 50 casein unit/g coagulated protein) was used to conduct a plate method using urokinase as a standard material. The liquid of the plasminogen activator was diluted with 0.067 M tris-HCl buffer solution (pH 8.0) containing 1% gelatin, 0.1 M sodium chloride and 0.1% sodium nitride. The concentration of the liquid of the activator showing the same dissolution window as 10 IU/ml of urokinase on the fibrin plate was set at 10 U/ml. When the measurement was made of the solution containing urokinase, an anti-urokinase IgG obtained from rabbits was added to the test solution so that the concentration thereof was 100 $\mu$g/ml.

When the desired yield or time is reached, the culture liquid is collected to recover the activator.

The recovery of the plasminogen activator can be achieved by any one of or a combination of an adsorption process, salting-out process, dialysis process, chromatography process and gel filtration process, which are normally applied for recovery of protein. Examples of such purification processes are fibrin Sephalose column chromatography using Sephalose having fibrin bonded thereto, CM Sephalose column chromatography using Sephalose having carboxymethyl group bonded thereto, lysine Sephalose column chromatography using Sephalose having lysine bonded thereto, ligand exchanging chromatography using zinc-chelated Sephalose, lectin column chromatography using Sephalose having Concanavalin A bonded thereto, antibody affinity chromatography using antibody which specifically combines with the plasminogen activator, and gel filtration using crosslinked dextran particles.

As an example of the purification process, the tissue culture liquid is adsorbed into a CM cephalose column equilibrated with a 20 mM acetate buffer solution (pH 4.0) containing 0.1% Tween 80 and 0.15 M sodium chloride. After being washed with a 20 mM acetate buffer solution (pH 4.0) containing 0.1% Tween 8.0 and 0.15 M sodium chloride, the column is treated with a 20mM tris-HCl buffer solution (pH 8.9) containing 0.1% Tween 80 and 1 M sodium chloride to effect an elution; whereby the solution of the part having the plasminogen activator activity is collected. The solution thus collected is dialyzed overnight at 4° C. against a 20 mM tris-HCl buffer solution containing 0.1 M potassium rhodanide, 0.1% Tween 80, and 0.05 M sodium chloride. The solution thus dialyzed is adsorbed into a lysine Sephalose column equilibrated with the same buffer solution. After being washed with an equilibrated buffer solution, the column is treated with a 20 mM tris-HCl buffer solution containing 0.05 M sodium chloride, 1 M potassium rhodanide, 0.2 M $\epsilon$-amino-n-caproic acid and 0.1% Tween 80 to effect an elution. The solution thus eluted is concentrated through hollow fibers for ultrafiltration, and then gel-filtrated through a column of Sephacryl S-200 to obtain the desired plasminogen activator.

The physicochemical properties of the plasminogen activator thus obtained are illustrated below:

(a) molecular weight: 63,000±10,000

The molecular weight measurement was effected by means of a gel filtration process using Sephadex G-150 equilibrated with a 0.01 M phosphate buffer solution (pH 7.0) containing 1.5 M sodium chloride, 0.1 M EDTA, 0.1 M arginine and 0.1% Tween 80. The measurement of molecular weight in unreduced state by the SDS (sodium dodecylsulphate) electrophoresis process indicated a molecular weight of about 70,000.

(b) isoelectric point: 7.0 to 8.5

An isoelectric point electrophoresis process using ampholyte was applied to effect a fractionation at the isoelectric point, whereby the isoelectric point was measured.

(c) affinity to fibrin

To 950 μl of a 0.2% plasminogen-free fibrinogen solution in physiological saline was added 20 μl of a 500 U/ml plasminogen activator solution obtained by the present invention. The admixture was allowed to stand at room temperature for 1 hour. The resulting fibrin was separated and collected from the admixture, dehydrated, and washed with physiological saline. The extraction of the activator in fibrin with 1 ml of a 2 M ammonium rhodanide solution showed that about 70% of the activator had been incorporated into fibrin. On the other hand, the tissue culture urokinase was not incorporated into fibrin at all.

(d) affinity to Concanavalin A 2 ml of the plasminogen activator (30 U/ml) obtained by the present invention was dissolved into physiological saline. The solution thus prepared was adsorbed into a column (0.5×4 cm) filled with Concanavalin A-Sephalose (manufactured by Pharmacia). The column was washed with a 1 M sodium chloride, with the result that almost 100% of the plasminogen activator was adsorbed.

(e) optimum pH value: 7 to 9.5

50 μl of the solution of the plasminogen activator in physiological saline was mixed with 50 μl of a 8 CU/ml physiological saline solution of plasminogen containing 10% glycerin and 100 μl of various buffer solutions containing a 0.10 M sodium chloride; the buffers being a 0.05 M citrate buffer solution (pH 5.0 or 6.0), a phosphate buffer solution (pH 6.0, 7.0 or 8.0) and a glycine-sodium hydroxide buffer solution (pH 8.0, 9.0, 10.0 or 11.0) (i.e., seven buffers, each at a different pH of 5.0, 6.0, 7.0, 8.0, 9.0, 10.0 or 11.0). The admixtures were preincubated at a temperature of 37° C. for 30 minutes. To the admixtures thus pre-incubated were added 500 μl of Boc-Glu-Lys-Lys-MCA dissolved in a 0.15 M tris-HCl buffer solution (pH 8.0). The admixtures were further incubated at a temperature of 37° C. for 15 minutes. 1 ml of acetic acid was added to the admixtures thus incubated to stop reaction. The resulting aminomethylcumarine was measured by fluorescence process to determine the optimum pH value. The results are shown in FIG. 1.

(f) reactivity with anti-urokinase specific antibody

Rabbits were immunized by the injection of purified urokinase (specific activity: 150,000 IU/mg protein) with Freund's complete adjuvant every 7 days in 35 days. Blood was collected from the rabbits and purified to obtain 50 μg/ml of a solution of anti-urokinase specific antibody. The solution of the anti-urokinase specific antibody and a 20 U/ml solution of plasminogen activator obtained by the present invention were mixed with each other in a mixing ratio of 1:1. The activity of the admixture was measured according to the above mentioned method. As a result, no activity drop was recognized.

On the contrary, the urokinase activity of the mixture of the solution of the anti-urokinase antibody and a 20 IU/ml urokinase solution as a control was 100% inhibited.

As described above, the plasminogen activator obtained by the present invention does not react with anti-urokinase antibody.

The plasminogen activator thus obtained can be applied not only for medicines as thrombolytic agent but also for chemicals for prevention of thrombus adapted to be bonded to artificial vein, artificial intestines or the like and diagnostic medicine for thrombus.

The process of the present invention is well suited for the stable mass production on the industrial scale of plasminogen activator which proves effective with less amount than familiar urokinase or streptokinase and has higher thrombolytic activity and less side effects than urokinase or streptokinase.

This invention will be further illustrated in the following examples:

EXAMPLE 1

500 g of well-minced beef was put into 1,000 ml of purified water. 12.5 ml of concentrated hydrochloric acid was added to the admixture. 6 g of pepsin was then added to the admixture. The admixture was allowed to effect digestion at a temperature of 37° C. for 2 days while being shaken occasionally. This digested liquid was heated to a temperature of 100° C. for 5 minutes. The liquid was filtered, and the filtrate was treated with sodium hydroxide to obtain pH value around neutrality (i.e., about 7.0). While maintained at a temperature of 45° C., the liquid was concentrated by means of a rotary evaporator. The liquid thus concentrated was then dried to obtain 130 g of a light-yellowish brown pepsin-decomposed beef peptone.

Next, the effect of the pepsin-decomposed beef peptone over normal diploid cells derived from human fetus lung (manufactured by Flow Laboratory) on the promotion of the production of the plasminogen activator was studied. A plastic laboratory dish (diameter: 100 mm) was planted with the normal diploid cells in a density of $7 \times 10^4$ cells/ml. 10 ml of Medium MEM (minimum essential medium: see Eagle H., Science, 130, 432, (1959)) containing 10% fetal calf serum was added to the dish as a culture medium. The dish thus prepared was then treated in air containing 5% carbon dioxide at a temperature of 37° C. to effect a full proliferation. The dish thus treated was washed with physiological saline. 20 ml of Medium 199 containing 1% (wt/v) of pepsin-decomposed beef peptone was added to the dish. The contents of the dish was sampled every 5 days for the measurement of the activity of the plasminogen activator. The results are shown in Table 1 along with that of a control experiment free of the pepsin-decomposed beef peptone. The medium containing the pepsin-decomposed beef peptone showed higher yield than that free of the peptone.

TABLE 1

|  | Yield (U/ml) | | | | |
|---|---|---|---|---|---|
|  | 5 | 10 | 15 | 20 | 25 (day) |
| Medium containing 1% (wt/v) peptone | 8 | 18 | 32 | 39 | 47 |
| Medium free of peptone | 0.3 | 0.6 | 1 | 1.2 | 1.5 |

EXAMPLE 2

Figure 2:
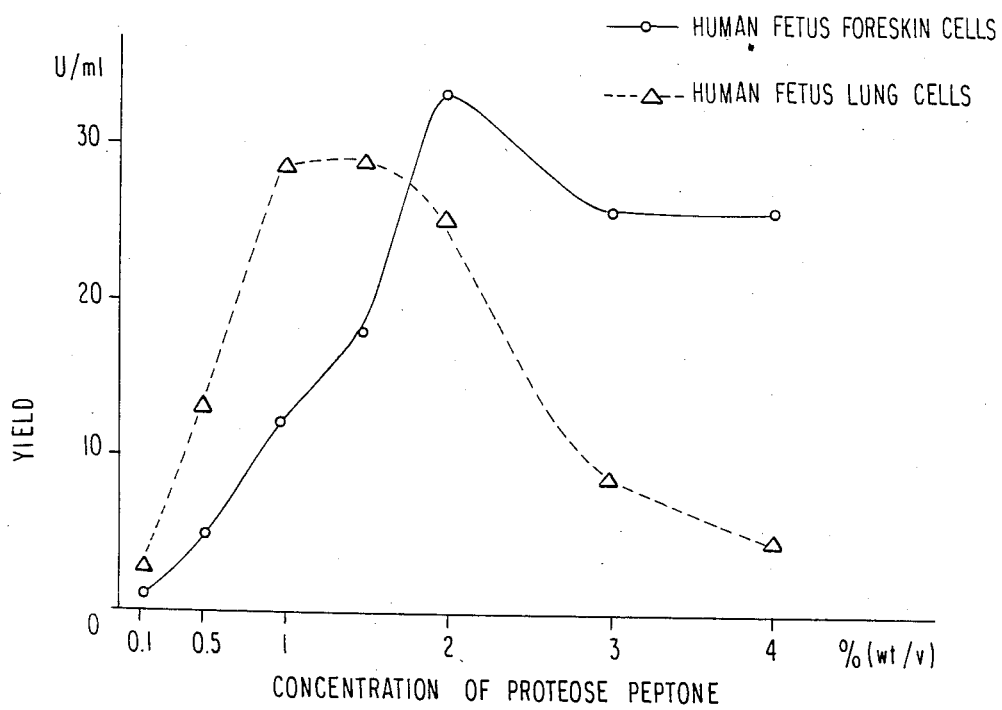
FIG. 2 is a graph showing the results of the measurement of the yield of the plasminogen activator in the culture liquid in Example 2.

Normal diploid cells derived from human fetus lung and human fetus foreskin (manufactured by Flow Laboratory) were proliferated as in Example 1. To these proliferated diploid cells was added Medium MEM with different concentrations of Proteose Peptone No. 3, which is a pepsin-decomposed animal meat peptone commercially available from Difco. The diploid cells were maintained in air containing 5% carbon dioxide at a temperature of 37° C. for 10 days. The results of the measurement of the activity of the plasminogen activator in the culture medium are shown in FIG. 2. A rapid increase of yield appears in the peptone content range of from 1 to 4% (wt/v).

EXAMPLE 3

In this example, the effect of different enzymatically-decomposed animal meat peptones over normal diploid cells derived from human fetus lung or human fetus foreskin on the promotion of the production of the plasminogen activator was studied.

84 g of pepsin-decomposed whale meat peptone was prepared from 500 g of whale meat as in Example 1.

110 g of pancreatin-decomposed beef peptone was obtained as follows:

500 g of minced beef was put into 1,000 ml of purified water. The admixture was treated with sodium carbonate to obtain a pH value of about 8. 15 g of pancreatin was added to the admixture. The admixture was then allowed to effect digestion at a temperature of 37° C. for 2 days. The liquid thus digested was treated as in Example 1 to obtain the peptone desired.

Various medium 199 containing 1% by weight of these peptones or various commercially available enzymatically-decomposed animal meat peptones were prepared. The above normal diploid cells were proliferated as in Example 1. To the diploid cells thus proliferated were added these culture mediums respectively. These culture medium were maintained in air containing 5% carbon dioxide at a temperature of 37° C. for 7 days to produce the plasminogen activator. The results of the measurement of the yield of the activator are shown in Table 2.

As control, the hydrolyzate of lactalbumin and polypeptone which had been not made from animal meats were used. Although these materials proved effective in the promotion of the production of the activator, the peptones made from animal meats proved far more effective.

TABLE 2

| Additive | Yield (U/ml) Human fetus lung | Human fetus foreskin |
|---|---|---|
| Nothing added | 0.4 | 0.3 |
| 1% (wt/v) Pepsin-decomposed beef peptone | 14.3 | 12.6 |
| 1% (wt/v) Pepsin-decomposed whale meat peptone | 10.6 | 14.2 |
| 1% (wt/v) pancreatin-decomposed beef peptone | 11.2 | 15.6 |
| 1% (wt/v) Proteose Peptone No. 1 (Difco) | 12.4 | 14.4 |
| 1% (wt/v) Proteose Peptone No. 2 (Difco) | 4.8 | 9.6 |
| 1% (wt/v) Proteose Peptone No. 3 (Difco) | 15.6 | 15.2 |
| 1% (wt/v) Proteose Peptone (Daigo Eiyo) | 4.9 | 4.6 |
| 1% (wt/v) lactalbumin | 2.8 | 2.4 |

TABLE 2-continued

| Additive | Yield (U/ml) Human fetus lung | Human fetus foreskin |
|---|---|---|
| hydrolyzate (Difco) 1% (wt/v) Polypeptone (Diago Eiyo) | 4.8 | 5.4 |

EXAMPLE 4

In this example, the effect of the pancreatin-decomposed beef peptone over various cells on the promotion of the production of the plasminogen activator is illustrated.

Specifically, various cells were subjected to a full proliferation in a plastic laboratory dish (diameter: 100 mm) according to the method of Example 1. The medium of the cells thus proliferated was replaced by Medium 199 to which 1% lactalbumin hydrolyzate or 1% pancreatin-decomposed beef peptone had been added. The medium was maintained in air containing 5% carbon dioxide at a temperature of 37° C. for 7 days. The results of the measurement of the yield of the activator are shown in Table 3.

TABLE 3

| Cells | Nothing added | 1% lactalbumin hydrolyzate | 1% pancreatin-decomposed beef peptone |
|---|---|---|---|
| Human fetus lung | 0.4 | 14.0 | 25.0 |
| Human fetus foreskin | 0.2 | 2.4 | 18.8 |
| Human fetus kidney | 0 | 0.1 | 3.0 |
| Human fetus skin | 0 | 0.2 | 3.6 |
| Human fetus small intestines (Flow Laboratory) | 0.2 | 1.6 | 5.4 |

EXAMPLE 5

A 12 liter spinner flask was planted with human fetus lung cells of a density $10^5$ cells/ml along with Cytodex I (beads carrier for cell culture; Pharmacia's registered trademark) of a concentration of 3 mg/ml. 8 liters of Medium MEM containing 10% fetal calf serum as a culture medium was added to the flask. The flask thus prepared was treated in air containing 5% carbon dioxide at a temperature of 37° C. while being rotated at a speed of 30 rpm to effect a suspension culture. The culture was effected for 6 days so that the cells were fully proliferated. The beads carrier to which the cells had adhered was washed with physiological saline and replaced by 8 liters of medium 199 containing 1% serum-free Proteose Peptone No. 3 (Difco). Another culture was effected with stirring at a rotation speed of 30 rpm. The medium liquid containing the plasminogen activator of the present invention was then recovered at the time of the replacement of the medium every 5 days.

10 liters of the thus obtained medium liquid containing the activator at the concentration of 35 U/ml was absorbed into a CM Sephalose column (1.5$\phi$ × 10 cm) equilibrated with a 20 mM acetate buffer solution (pH 4.0) containing 0.1% Tween 80 and 0.15 M sodium chloride. After being washed with a 20 mM acetate buffer solution (pH 4.0) containing 0.1% Tween 80 and 0.15 M sodium chloride, the CM Sephalose column was treated with a 20 mM tris-HCl buffer solution (pH 8.9) containing 0.1% Tween 80 and 1 M sodium chloride to effect an elution, whereby the solution of the part having the plasminogen activator activity was recovered in an amount of 103 ml. The solution thus recovered was dialyzed overnight at a temperature of 4° C. against 5 liters of a 20 mM tris-HCl buffer solution containing 0.1 M potassium rhodanide, 0.1% Tween 80, and 0.05 M sodium chloride. The solution thus dialyzed was adsorbed into a lysine Sephalose column (2.6φ×12 cm) equilibrated with the same buffer solution. After being washed with an equilibrated buffer solution, the lysine Sephalose column was treated with a 20 mM tris-HCl buffer solution containing 0.05 M sodium chloride, 1 M potassium rhodanide, 0.2 M ε-amino-n-caproic acid and 0.1% Tween 80 to effect an elution. 130 ml of the liquid thus eluted was concentrated to 12 ml through hollow fibers for ultrafiltration. The liquid thus concentrated was gel-filtered through a column (2.6φ×94 cm) of Sephacryl S-200 to recover 45 ml of the solution of the part having the plasminogen activator activity of the present invention. The plasminogen activator solution thus obtained had a concentration of 4,800 U/ml and showed a specific activity of 38,000 U/mg protein.

While the invention has been described in detail and with reference to specific embodiments thereof, it will be apparent to one skilled in the art that various changes and modifications can be made therein without departing from the spirit and scope thereof.

What is claimed is:

1. A process for the preparation of a plasminogen activator, which comprises bringing normal diploid cells derived from human bodies capable of producing the plasminogen activator into contact with a solution containing an enzymatically-decomposed animal meat peptone, the plasminogen activator having the following properties:
    (a) molecular weight: 63,000±10,000;
    (b) isoelectric point: 7.0 to 8.5;
    (c) affinity to fibrin: present;
    (d) affinity to Concanavalin A: present;
    (e) optimum pH: 7 to 9.5; and
    (f) no reactivity with anti-urokinase specific antibody.

2. A process as in claim 1, wherein the peptone concentration of said solution containing the enzymatically-decomposed animal meat peptone is from 0.1 to 4% (wt/v).

3. A process as in claim 1, wherein said normal diploid cells are cells derived from human lung or human foreskin.

4. A process as in claim 1, wherein the peptone concentration of said solution containing the enzymatically-decomposed animal meat peptone is from 0.1 to 2% (wt/v).

5. A process as in claim 2, wherein said normal diploid cells are cells derived from human lung or human foreskin.

6. A process as in claim 4 wherein said normal diploid cells are cells derived from human lung or human foreskin.

* * * * *